US00PP25760P3

(12) United States Plant Patent
Rotolante

(10) Patent No.: US PP25,760 P3
(45) Date of Patent: Jul. 28, 2015

(54) ***STROMANTHE* PLANT NAMED 'ROTOLANTE10'**

(50) Latin Name: *Stromanthe stromanthoides*
Varietal Denomination: ROTOLANTE10

(71) Applicant: SILVER KROME GARDENS, INC., Homestead, FL (US)

(72) Inventor: Denis Rotolante, Homestead, FL (US)

(73) Assignee: SILVER KROME GARDENS, INC., Homestead, FL (US)

( * ) Notice: Subject to any disclaimer, the term of this patent is extended or adjusted under 35 U.S.C. 154(b) by 123 days.

(21) Appl. No.: 13/815,093

(22) Filed: Jan. 30, 2013

(65) Prior Publication Data

US 2014/0215672 P1 Jul. 31, 2014

(51) Int. Cl.
*A01H 5/12* (2006.01)
*A01H 5/02* (2006.01)

(52) U.S. Cl.
USPC ..... Plt./373
CPC ..... *A01H 5/02* (2013.01)

(58) Field of Classification Search
USPC ..... Plt./373
See application file for complete search history.

(56) References Cited

PUBLICATIONS

Welcome to *Stromanthe* 'Charlie', blog by Craig Morell, Apr. 11, 2014, downloaded from http://pinecrestgardenguy.blogspot.com/2014/04/stromanthe-charlie html.*
Beautifully Variegated *Stromanthe,* Jan. 18, 2013, downloaded from http://www.newplantsandflowers.com/beautifully-variegated-stromanthe/.*

* cited by examiner

*Primary Examiner* — Anne Grunberg
(74) *Attorney, Agent, or Firm* — Jondle & Associates, P.C.

(57) ABSTRACT

A new and distinct variety of *Stromanthe* plant named 'ROTOLANTE10' particularly distinguished by its bright, broad leaf variegation, compact growth habit, short petioles, and tolerance to a broad range of light regimes, is disclosed.

2 Drawing Sheets

Genus and species: *Stromanthe stromanthoides.*
Variety denomination: 'ROTOLANTE10'.

BACKGROUND OF THE NEW PLANT

The present invention relates to a new and distinct *Stromanthe* variety designated 'ROTOLANTE10' and botanically known as *Stromanthe stromanthoides*. The predecessor plant of 'ROTOLANTE10' was collected in South America and then placed into tissue culture where somaclonal variations occurred. The plants produced by tissue culture had variations, which were then used in selection by the inventor. The new *Stromanthe* was discovered and selected by the inventor from a naturally occurring, single plant mutation of *Stromanthe* within a population of *Stromanthe* plants in a controlled greenhouse environment in Homestead, Fla. This single plant was selected for further evaluation and for asexual propagation in Homestead, Fla. based on its bright leaf variegation pattern, compactness of growth and ease of growth.

The new variety was first propagated via vegetative cuttings in the summer of 2002 in Homestead, Fla. and has been asexually reproduced repeatedly by vegetative cuttings and tissue culture in Homestead, Fla. for 12 generations. 'ROTOLANTE10' has been found to retain its distinctive characteristics through successive asexual propagations by vegetative cuttings and tissue culture.

Plant Breeder's Rights for this variety have not been applied for. 'ROTOLANTE10' has not been made publicly available more than one year prior to filing of this application

SUMMARY OF THE INVENTION

The following are the most outstanding and distinguishing characteristics of this new cultivar when grown under normal horticultural practices in Homestead, Fla.

1. Bright, broad leaf variegation;
2. Compact growth habit with short petioles; and
3. Tolerance to a broad range of light regimes.

DESCRIPTION OF PHOTOGRAPH

This new *Stromanthe* plant is illustrated by the accompanying photographs. The colors shown are as true as can be reasonably obtained by conventional photographic procedures. The photographs are of 1-year old plant propagated by vegetative cuttings from rhizomes.

DESCRIPTION OF THE NEW CULTIVAR

Figure 1:
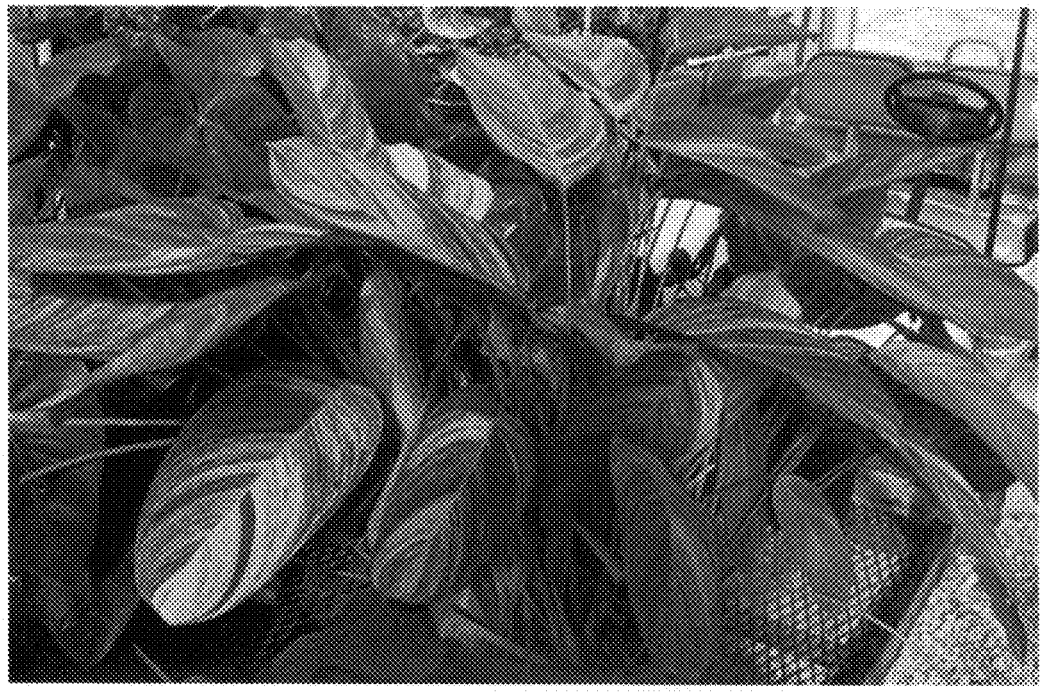
FIG. 1 shows a whole plant.
Figure 2:
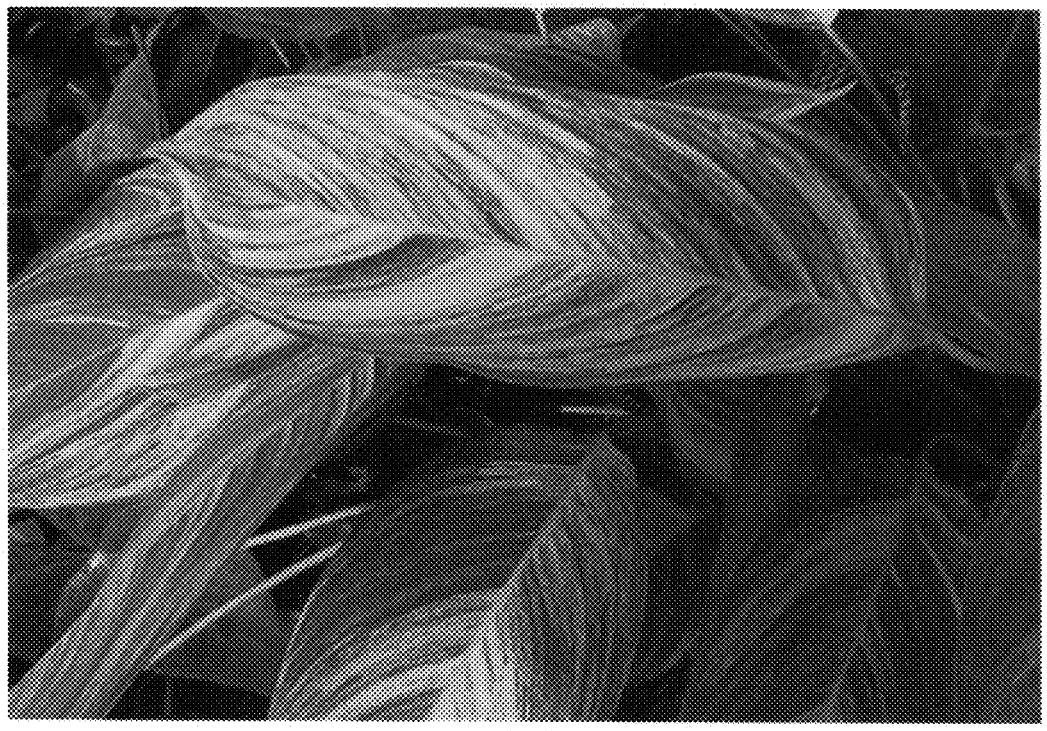
FIG. 2 shows a close up the mature foliage.
Figure 3:
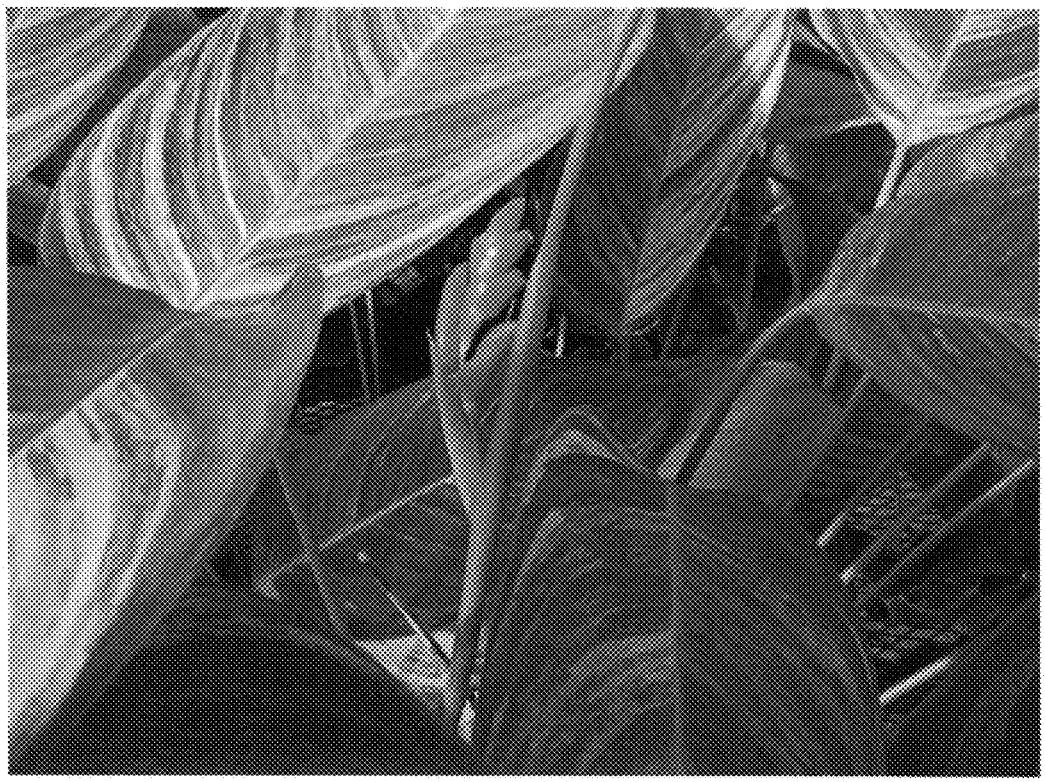
FIG. 3 shows a close up of the mature foliage and a mature bract.

The following detailed description sets forth the distinctive characteristics of 'ROTOLANTE10'. The data which define these characteristics were collected from asexual reproductions carried out in Homestead, Fla. The plant history was taken in the summer of 2012 on one-year old plants grown in 15 cm pots. The plants were grown in a greenhouse covered in six mill polyethylene film and 73% shade cloth. Color readings were taken under natural light. Color references are primarily to The R.H.S. Colour Chart of The Royal Horticultural Society of London (R.H.S.), Third Edition (1995).

DETAILED BOTANICAL DESCRIPTION OF THE NEW PLANT

Classification:
- *Family*.—Marantaceae.
- *Botanical name*.—*Stromanthe stromanthoides*.
- *Common name*.—*Stromanthe*.

Growth:
- *General*.—Tropical potted plant; plant is suitable for use in shaded tropical and frost-free landscapes.
- *Container size*.—4 liter (15.0 cm diameter) and 12 liter (25.5 cm diameter).

Plant description:
- *Form*.—Erect.
- *Life cycle*.—Herbaceous perennial herb.
- *Habit*.—Upright and branching from the rhizomes at the base of the plant.
- *Vigor*.—Medium to fast growth rate.
- *Height* (*from top of soil*).—35.0 cm.
- *Width* (*horizontal plant diameter*).—40.0 cm.
- *Time to produce a finished plant*.—2 liter container (6 inch or 15 cm in diameter): 6 months. 12 liter container (10 inch or 25 cm in diameter): 11 to 12 months.
- *Time to initiate and develop roots from unrooted cuttings*.—2 to 4 weeks.
- *Root description*.—Primary adventitious roots dominant from the rhizome branching to secondary rootlets.
- *Propagation method*.—Tissue culture and vegetative cuttings.

Branches:
- *Number*.—4 to 6.
- *Length*.—Variable depending upon age.
- *Lateral branch diameter*.—1.5 cm.

Stems (rhizomes):
- *Description*.—Cylindrical, round in traverse section.
- *Aspect*.—Horizontal, underground rhizome becoming upturned, vertical at tip.
- *Strength*.—Thick, tough and fibrous.
- *Internode length*.—1.0 cm to 2.0 cm.
- *Color*.—RHS 158D.

Leaves:
- *Arrangement*.—Alternate, closely spaced in vertical ranks, rosette, with 1 to 3 per lateral branch depending on age of the branch.
- *Shape*.—Simple, elliptical.
- *Apex*.—Obtuse with acuminate tip.
- *Base*.—Asymmetrical, obtuse.
- *Margin*.—Entire; very slightly concaving along the margins.
- *Length*.—15.0 cm to 28.0 cm.
- *Width*.—6.0 cm to 11.0 cm.
- *Color* (*both immature and mature leaves*).—Upper surface: RHS 158D to RHS 142A. Lower surface: RHS 158D to RHS 142D.
- *Venation color* (*both upper and lower surfaces*).—RHS 158D.
- *Variegation* (*both immature and mature leaves*).—Upper surface: RHS 158D to RHS 142A. Lower surface: RHS 158D to RHS 142D.
- *Petiole*.—Aspect: Upright. Length: 15.0 cm to 30.0 cm. Diameter: 0.2 cm to 0.4 cm. Texture: Smooth. Color: RHS 158D.
- *Geniculum*.—Aspect: The orientation of the leaf to the petiole is variable, as the geniculum bends; during the night and early morning the geniculum is straight and the leaf is held nearly vertical above the foliage; during the day, the geniculum is bent and the leaf curves outward. Length: 1.0 cm to 2.0 cm. Diameter: 0.3 cm to 0.5 cm. Color: RHS 158D. Texture: Smooth.

Leaf sheath:
- *Length*.—5.0 cm to 10.0 cm.
- *Diameter*.—0.5 cm.
- *Apex*.—Acute.
- *Texture*.—Smooth.
- *Color*.—RHS 158D.

Inflorescence:
- *Arrangement*.—Sparingly arising from the axils of the leaves.
- *Time of year observed*.—Spring and summer.
- *Quantity of inflorescence per plant*.—1 to 2.
- *Fragrance*.—Absent.
- *Lastingness of inflorescence*.—21 days.
- *Peduncle*.—Length: 15.0 cm to 25.0 cm. Diameter: 0.2 cm to 0.4 cm. Angle: Upright to 15 degrees from center. Strength: Medium strong. Texture: Smooth. Color: RHS 158D.
- *Bracts*.—Aspect: Overlapping. Shape: Elliptical, concave. Apex: Obtuse. Base: Obtuse. Margin: Entire. Texture: Smooth. Length: 1.5 cm to 2.0 cm. Width: 1.0 cm to 1.5 cm. Color: Immature (both upper and lower surface): RHS 24A. Mature (both upper and lower surface): RHS 24A. Flowers: Small, white insignificant tubular flower protruding from a bract on the terminal inflorescence.

Fruit and seed set: Has not been observed.

Disease and insect resistance: Resistance to leaf spotting fungal pathogens.

Hardiness zones: USDA 10 to 11.

Drought tolerance: Moderate resistance to leaf burning resulting from too little water or water high in soluble salts.

COMPARISON WITH PARENTAL AND COMMERCIAL CULTIVARS

'ROTOLANTE10' can be distinguished from its antecedents in that 'ROTOLANTE10' has a brighter leaf variegation pattern, more compactness of growth and more ease of growth.

'ROTOLANTE10' can be distinguished from the commercial cultivar *Stromanthe* plant named 'Valmic' (U.S. Plant Pat. No. 15,475) in that 'ROTOLANTE10' has orange bracts with insignificant flowers and green coloration on the lower leaf surface, whereas 'Valmic' has red bracts with small white flowers and red coloration on the lower leaf surface. Additionally, 'ROTOLANTE10' has broader leaves, longer petioles and a more open appearance than 'Valmic'.

I claim:

1. A new and distinct variety of *Stromanthe* plant named 'ROTOLANTE10', as illustrated and described herein.

* * * * *